United States Patent [19]

Grace et al.

[11] Patent Number: 4,847,783
[45] Date of Patent: Jul. 11, 1989

[54] GAS SENSING INSTRUMENT

[76] Inventors: Richard Grace, 6373 Douglas St., Pittsburgh, Pa. 15213; Alberto M. Guzman, 114 Doray Dr., Pittsburgh, Pa. 15237; Marc A. Portnoff, 160 Robinson St., Pittsburgh, Pa. 15213; David A. Purta, 317 Stratford Ave., Suite 2, Pittsburgh, Pa. 15232; Paul D. Runco, 6009 Walnut St., Pittsburgh, Pa. 15206; John G. Tabacchi, 128 Fourth St., Oakmont, Pa. 15139

[21] Appl. No.: 54,865

[22] Filed: May 27, 1987

[51] Int. Cl.$^4$ ............................................. G06F 15/42
[52] U.S. Cl. ..................................... 364/497; 73/23; 422/98
[58] Field of Search ........................... 73/19, 23, 27 R; 340/634; 364/497, 498; 422/98

[56] References Cited

U.S. PATENT DOCUMENTS

| | | | |
|---|---|---|---|
| 4,347,732 | 9/1982 | Leary | 73/23 |
| 4,453,151 | 6/1984 | Leary et al. | 422/98 X |
| 4,457,161 | 7/1984 | Iwanaga et al. | 73/23 |
| 4,541,988 | 9/1985 | Tozier et al. | 422/98 X |
| 4,542,640 | 9/1985 | Clifford | 73/23 |
| 4,567,475 | 1/1986 | Bukowiecki et al. | 422/98 X |
| 4,638,443 | 1/1987 | Kaneyasu et al. | 364/497 |
| 4,670,405 | 6/1987 | Stetter et al. | 422/98 X |

OTHER PUBLICATIONS

"A Monolithic Gas Flow Sensor with Polymide as Thermal Insultator", Goran N. Stemme, Department of Solid State Electronics, Chalmers University of Technology, Gothenburg, Sweden.
"Development of a Hydrogen Sulfide Sensor, a Case Study", Sensor Expo Proceedings 1986, James L. Youngblood, Jun. 20, 1986.
"Olfactory Detection Using Integrated Sensor", Akira Ikegami and Masayoshi Kaneyasu, 1985 I.E.E.E.
"The Use of Multi-Sensors Systems in Monitoring Hazardous Atmosphers", B. Bott and T. A. Jones, 1985 B.C.C.
"Multispecies Integrated Electrochemical Sensor with On-Chip CMOS Circuitry", I. Lauks, J. Van der Spiegel, W. Sansen and M. Steyaert, 1985 I.E.E.E.
"A Thick-Film Multi-Layered Oxygen Sensor", S. J. Pace, P. P. Zarzycki, R. T. McKeever and L. Pelosi, 1985 I.E.E.E.
"Effects of Tetraethyl Orthosilicate Binder on the Characteristics of $SnO_2$ Ceramic Type Semiconductor Gas Sensor", S. Yasunaga, S. Sunahara and K. Ihokura, 1985 I.E.E.E.
"Multidimensional Sensors for Gas Analysis", R. Miller, E. Lange and A. Hinterstocker, 1985 I.E.E.E.
"Selective Detection of Chemicals Using Energy Modulated Signals", Joseph R. Stetter and Takaaki Otagawa, 1985 I.E.E.E.
"Alarm Detector of Gas Leaking with the Intelligentization", Proceeding of the 2nd International Meeting on Chemical Sensors, T. Oyabu, Y. Ohta, and T. Kurobe, Bordeaux, France, Jul. 7-10, 1986.
"Characterization of Multicomponent Gas Mixtures Via Liquid Coated/Piezoelectric Quartz Crystal Detectors", Proceedings of the 2nd International Meeting on Chemical Sensors, H. E. Hager, Peter D. Verge, and J. D. S. Danielson, Bordeaux, France, Jul. 7-10, 1986.
"A Microcomputer Controlled System for Characterizing Semiconductor Gases", Laboratory Practice, vol. 32, No. 6, Jun. 1983 by B. Bott and T. A. Jones.

Primary Examiner—Gary Chin
Assistant Examiner—Edward R. Cosimano
Attorney, Agent, or Firm—Ingersoll Buchanan

[57] ABSTRACT

A gas sensing instrument provides programmable control of the operating temperatures of an array of gas sensors for the detection of target gases in air. The control facilitates precise temperature setpoint resolution. The gas sensors in the array have an improved construction density with reduction in size and an extended operating life provided by reduced power consumption. A programmable circuit functions as a programmable-resistor temperature controller in a Wheatstone bridge configuration. A multiplying digital to analog converter circuit controls the ratio of voltage to current that functions as a resistance equivalent. The programmable circuit is interfaced with a computer to provide selectable temperature control for at least 256 setpoints.

20 Claims, 6 Drawing Sheets

GAS SENSING INSTRUMENT

BACKGROUND OF THE INVENTION

1. Field of the Invention

This invention relates to method and apparatus for sensing gases in air and more particularly to an array of metal oxide semiconductor gas sensors operated at controlled preselected temperatures to generate electrical responses which are processed by a microcomputer to accurately determine the respective concentrations of a plurality of gases in air.

2. Description of the Prior Art

As disclosed in U.S. Pat. No. 4,542,640 an array of nonselective semiconductor gas sensors are combined with a measurement and signal processing system to determine simultaneously and selectively the presence and concentration of several gases in ambient air. The method utilizes a set of nonlinear model equations, one equation for each gas sensor, which quantitatively relate the electrical response of each sensor to the concentration of the gases. Each model equation is characterized by a set of numerical parameters which describe the respective sensitivities of a particular sensor to each gas. Once the value of these parameters has been determined, gas detection is performed by a computation algorithm which transforms the measured responses of the sensors into a representation of the gas concentrations. The algorithm produces the value of gas concentrations most consistent with the model equations and with the measured sensor responses.

Due to the nonlinear nature of the model equations employed in U.S. Pat. No. 4,542,640 deviations of the sensor resistances from the values predicted by the model equations result in substantial inaccuracies in the measured gas concentrations. Such deviations can result from uncontrolled temperature fluctuations of the sensors, from slow changes over time of the sensor characteristics, or from the presence of unanticipated interference gases. Thus there is a need to provide a gas detection system that reliably and accurately detects several gases simulaneously in air in a compact and portable configuration that can be powered by conventional storage batteries.

The method for gas detection disclosed in U.S. Pat. No. 4,542,640 is known as deconvolution and is applicable to the detection of a particular set of target gases if one or more of the sensors responds to each gas. Also there must be at least as many sensors having distinct response characteristics as there are target gases. Deconvolution is also applicable in the case where gases other than the target gases are present, provided that none of the sensors respond appreciably to any of the interference gases. Thus there is a further need for a gas detection method and apparatus in which the sensitivities of each sensor to the respective gases can be selectively increased or decreased.

As disclosed in U.S. Pat. No. 4,457,161 an array of metal oxide semiconductor gas sensors fabricated by thick film printing processes are suitable for incorporation with a microcomputer in a gas detection instrument. The gas sensors formed on an insulating substrate are heated by an integral thick film heating element to an operating temperature in the range between about 400° to 450° C.

As disclosed in the publication entitled "A Microcomputer Controlled System For Characterizing Semiconductor Gases", *Laboratory Practice*, June 1983, Volume 32, No. 6 by B. Bott and T. A. Jones, a computer controlled system for characterizing semiconductor gas sensors employs a circuitry for maintaining a gas sensor at a programmable constant temperature. The circuit uses the out of balance signal of a Wheatstone bridge to maintain the resistance of the platinum heater, and hence the substrate temperature at a constant value. A particular resistor or resistor combination in conjunction with the circuitry regulates the operating point temperature of the semiconductor gas sensors. The temperature setpoints are distinct and are determined by the limited number of adjustable resistors, for example eight temperature setpoints would be available for a given temperature range. With this arrangement sensor operating temperatures can be maintained independent of ambient temperature or gas flow conditions. However, the discrete resistors and relays place certain limits on the size, cost, and reliability of the instrumentation.

Overall the accuracy of the known deconvolution method depends on the accuracy with which the model equations describe the actual gas sensor response. Because of the nonlinear nature of the gas response characteristics of semiconductor gas sensors, small deviations of the actual sensor responses from the predetermined model responses can produce significant errors in the deconvoluted gas concentrations. Such errors will not occur if the sensor response parameters remain constant and equal to the predetermined values. Because these parameters are temperature dependent, it is desirable to have a stable and reproducible temperature.

While it is known to simultaneously and selectively determine the presence and concentration of a number of target gases in ambient air and control the temperature at which the gas sensors operate, there is need to provide a computer operated temperature controller having the capability of an increased number of selectable setpoint temperatures.

SUMMARY OF INVENTION

In accordance with the present invention there is provided an instrument for simultaneously determining the concentrations of a plurality of gases present in air that includes a microcomputer. A plurality of semiconductor gas sensing elements are provided at least equal in number to the number of gases to be detected. The gas sensing elements each have a predetermined response characteristic differing from the response characteristic of the other said gas sensing elements in response to at least one of the gases to be detected. Temperature control means, responsive to said microcomputer, for maintaining each of the gas sensing elements at a selected one of a plurality of operating temperatures. Measurement means connected to each of the gas sensing elements generates a plurality of electrical signals representing the response of the each of the respective gas sensing elements to the gases to be detected. The measurement means is electrically connected to the microcomputer. The microcomputer includes means for converting the signals from the measurement means to a digital representation of the concentration of the gases detected in the air.

Accordingly, the principal object of the present invention is to provide a gas sensing instrument for simultaneously and accurately determining the concentrations of a plurality of gases in air using an array of temperature-controlled metal oxide semiconductor gas sensing elements.

A further object of the present invention is to provide method and apparatus for operating an array of gas sensors at a preselected temperature appropriate for measuring the concentrations of a plurality of gases in air.

Another object of the present invention is to provide a method and apparatus for analyzing the concentrations of target gases in air by characterizing the electrical responses of a plurality of gas sensing elements based on resistance measurements.

Another object of the present invention is to provide a gas detecting instrument that includes a programmable resistance measurement circuit such that any one of a number of preselected voltages can be supplied to electrodes of a plurality of gas sensors in order to enhance the responsiveness, stability and selectivity of the gas sensors.

An additional object of the present invention is to provide in a gas detecting instrument a programmable temperature controller for operating each of the plurality of gas sensors at any one of a number of selectable temperatures and bringing the gas sensors to a preselected operating temperature in a reduced period of time.

Additionally, another object of the present invention is to provide a method for detecting a plurality of gases in air which provides means for sounding an alarm and displaying the concentrations of the gases being measured in air.

These and other objects of the present invention will be more completely disclosed and described in the following specification, the accompanying drawings, and the appended claims.

DESCRIPTION OF THE PREFERRED EMBODIMENTS

Microcomputer

Figure 1:
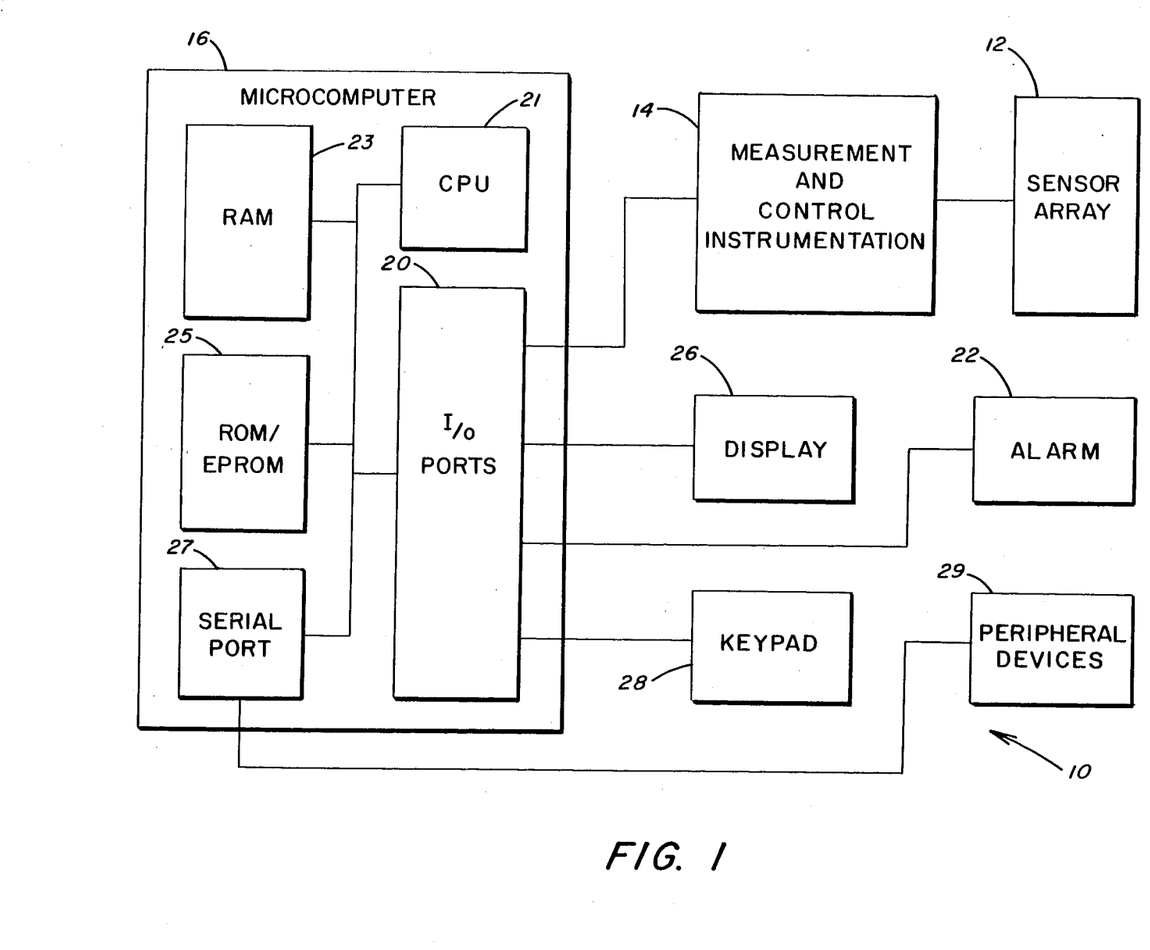
FIG. 1 is a diagrammatic illustration of a gas detecting instrument in accordance with the present invention.

Referring to the drawings and particularly to FIG. 1, there is illustrated a gas detection instrument generally designated by the numeral 10 that includes a gas sensor array 12 electrically connected to a measurement and control instrumentation 14. The instrumentaton 14 is connected to a microcomputer 16 through a parallel input/output port 20. A keypad 28 connected to the input/output port 20 serves as an input terminal by which the user may select a particular gas or gases to be identified. The microcomputer 16 is connected to a suitable audio/visual alarm 22 through the input/output port 20 for signaling an alarm condition indicating a concentration of a target gas above a threshold amount. An alpha/numeric output display 26 also connected to the input/output port 20 provides a quantitative indication of the measured concentration of the selected gas.

The microcomputer 16 includes the components of a central processing unit (CPU) 21, RAM 23, ROM/EPROM 25, and serial port 27 connected to the input/output port 20. The serial port 27 is also connected to selected peripheral devices 29 and is capable of interfacing to RS-232 standards. The serial port 27 allows communication with other equipment for calibration, testing, evaluation, and remote data logging. In this manner the microcomputer is also interfaced with process control or with an industrial monitoring system. The microcomputer 16 provides a display update of the gas concentrations every 30 seconds or faster and begins execution automatically upon powering on the gas detection instrument 10.

An example of a suitable microcomputer 16 in accordance with the present invention is the BCC52 manufactured by Micromint, Inc. It utilizes an Intel 8052AH-Basic microcontroller chip containing a ROM resident 8k byte Basic interpreter. The BCC52 single board computer/controller includes the 80528AH microprocessor, 48k bytes of RAM/EPROM, a 2764/128 EPROM programmer, three parallel ports (8 bits each), a serial terminal port with autobaud rate selection, a serial printer port, and a bus compatible with expansion boards.

The Basic interpreter is optimized for the particular chip architecture and has a powerful array of functions and floating-point mathematics. The capability exists to link customized assembly level machine-code routines to better optimize speed-critical algorithms. Automatic program execution at power up is thus easily implemented.

User Interface

The user interface illustrated in FIG. 1 includes the visual and audio alarms 22, the keypad 28 and the alpha/numeric display 26. The keypad 28 has keys numbered 0 through 9 as well as preprogrammed function keys. In a preferred embodiment 16 keys are arranged in a 4×4 matrix. The display is a liquid crystal display, LCD, that can display two lines of twenty-four alpha/numeric characters. The display is used to (1) display the sensed and computed simultaneous gas concentrations in parts per million, (2) to display "SAFE" and "HAZARD" status conditions, and (3) to prompt and display user keypad entry. The alarm 22 generates either audible or visual warnings of dangerous gas concentrations. The alarm limits are user-programmable and are set by pressing a function key and then responding to LCD prompts by using numeric key entry.

Generally the microcomputer 16 accepts input data from the user. For example, the user identifies a particular gas or gases to be sensed and specifies the interference gases likely to be encountered. Through the microcomputer 16 the operating temperatures of the respective sensors in the array 12 are set to appropriate values. The microcomputer 16 then measures the sensor resistances and converts the resistance values to a representation of the target gas concentrations using a signal processing algorithm known as the deconvolution algorithm. The microcomputer 16 then communicates to the user the gas concentration values and actuates the alarm 22 if pre-established threshold values for the concentrations are exceeded. The microcomputer 16 maintains in non-volatile memory the numerical model parameters for describing the response of each gas sensor in the array 12 to each gas when operating at a selected temperature.

Measurement and Control Instrumentation

The measurement and control instrumentation 14 shown in FIG. 1 serves as the interface between the microcomputer 16 and the gas sensor array 12. In operation the instrumentation 14 maintains the temperatures of the respective sensors at specific temperatures independent of ambient conditions, and allows the individual sensor temperatures to be selected by the microcomputer 16. This is achieved by incorporating within the instrumentation 14 an integrated circuit digital to analog converter (DAC) which acts as a programmable resistance in the Wheatstone bridge temperature control circuit of each film heater. In addition the instrumentation 14 maintains a preselected voltage across each sensor in the array 12 and allows the microcomputer 16 to measure the electrical current in each sensor element. Accordingly, the sensor resistance is calculated as the ratio of voltage to current. The voltage is selected by the microcomputer 16 in such a way that excessive sensor current is avoided.

Figure 2:
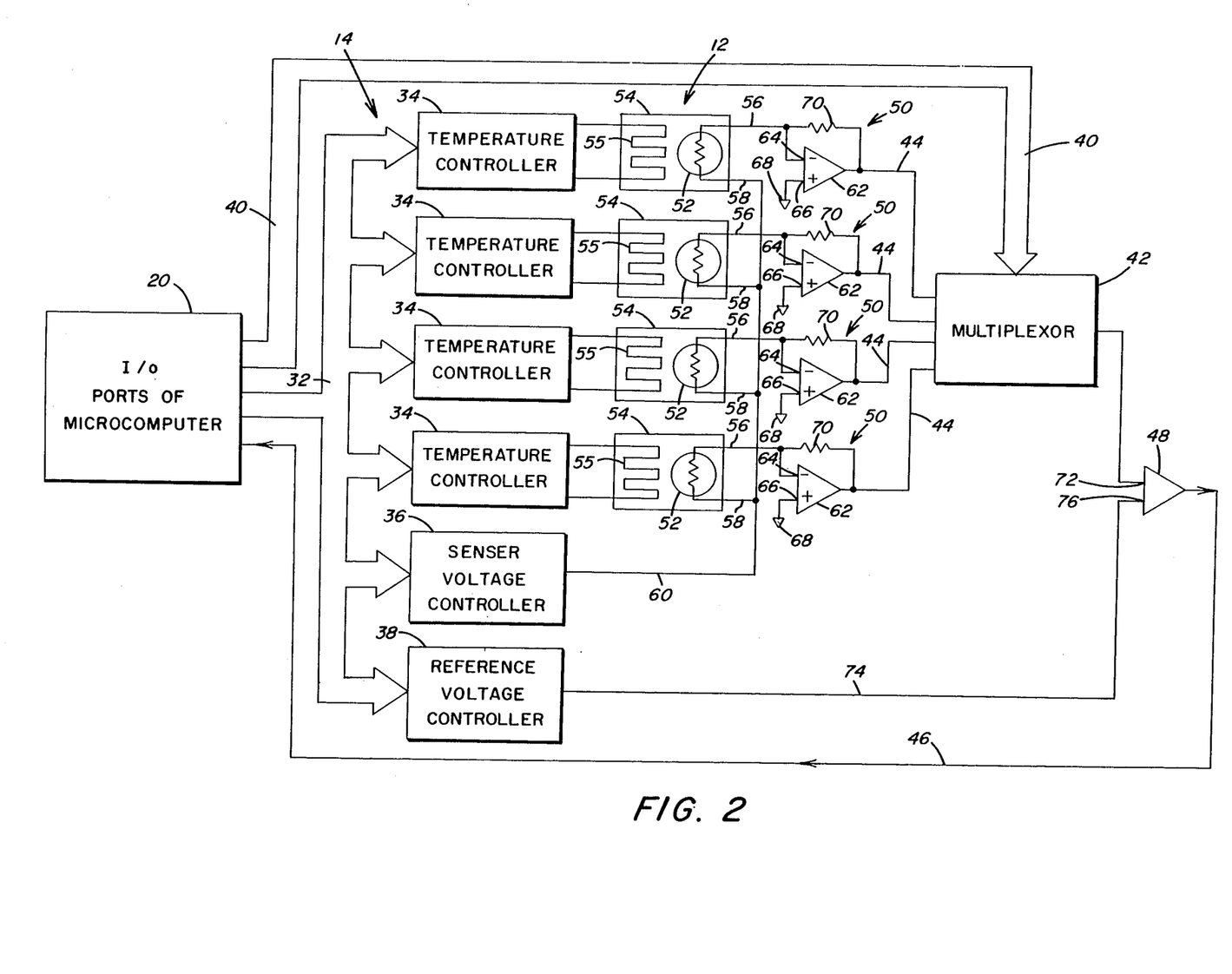
FIG. 2 is a schematic illustration of a plurality of gas sensors and the instrumentation for maintaining the sensors at a preselected temperature and measuring the gas sensor resistances.

Now referring to FIG. 2 there is schematically illustrated the parallel input/output ports 20 of microcomputer 16, the sensor array 12, and the measurement and control instrumentation 14 shown in FIG. 1. Parallel input/output lines 32 transfer data from microcomputer 16 to a plurality of programmable temperature controllers 34, a programmable sensor voltage controller 36, and a programmable reference voltage controller 38. The controllers 34, 36 and 38 comprise the measurement and control instrumentation 14 illustrated in FIG. 1. Other parallel input/output lines 40 from the input/output port 20 provide input to an integrated circuit multiplexor 42. The multiplexor 42 passes a selected one of the voltage signals from input lines 44 to the input of a comparator 48. A single input/output line 46 transmits the output signal of the comparator 48 to the input/output ports 20 of the microcomputer 16.

Resistance Measurement

As illustrated in FIG. 2, each electrode 56 of the respective sensors is connected to a feedback control circuit 50, and a second electrode 58 is connected to conductor 60 which is in turn connected to the programmable sensor voltage controller 36. The feedback control circuit 50 associated with each gas sensor 52 includes an amplifier 62 having a negative input terminal 64 connected to electrode 56 and a positive input terminal 66 connected to ground 68. A resistor 70 is connected across the input terminal 64 and the output of the amplifier 62. The output terminal of each amplifier 62 is connected by lines 44 to the multiplexor 42.

The programmable sensor voltage controller 36 applies a preselected voltage, for example a negative 2 volts, to the respective sensor electrodes 56 and 58. The currents in each sensor 52 are converted to equivalent voltage signals by feedback resistors 70 and amplifier 62. A signal representative of a reference voltage from the reference voltage controller 38 is transmitted by conductor 74 to a second input terminal 76 of the comparator 48. With this arrangement once the selected voltages are applied to the sensor electrodes 56 and 58, the multiplexor 42 selectively passes the voltages from the amplifiers 62 through to the comparator 48. Alternatively, a suitable integrated circuit analog to digital converter may replace comparator 48 and reference voltage controller 38.

The reference voltage controller 38 progressively increases the voltage as input to terminal 76 of comparator 48. The output of comparator 48 remains low until the voltage from controller 38 is equal to the voltage applied to the comparator input terminal 72 from the respective gas sensors 52 and corresponding feedback control circuits 50. At the point where the input voltage applied to terminals 72 and 76 of comparator 48 are equal, the comparator 48 switches its output voltage high to generate an output signal through conductor 46 to the input/output port 20 of the microcomputer 16. Once the voltages applied to the comparator 48 and terminals 72 and 76 are equal, the ramping of the reference voltage controller 38 is terminated. The value of this voltage is proportional to the electrical current in the selected gas sensor 52. For a fixed sensor voltage across the respective sensor, the resistance of the sensor is inversely proportional to the current that flows through the sensor. Therefore, the computer 16 can calculate the resistance of the gas sensor 52. Filtering capacitors may be connected in parallel with reference resistors 70 to reduce electrical noise.

Figure 3:
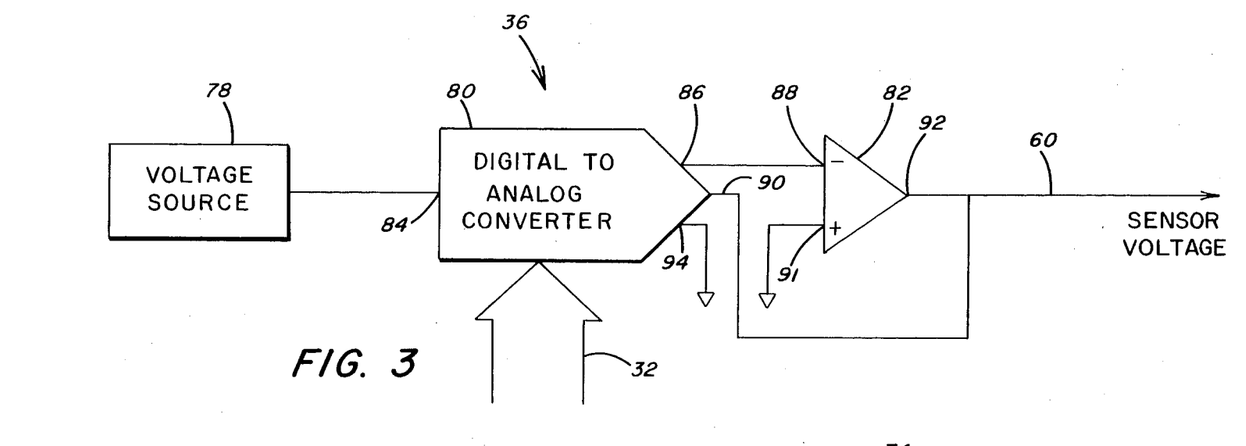
FIG. 3 is a diagrammatic illustration of the apparatus for controlling the voltage applied to each gas sensor.
Figure 4:
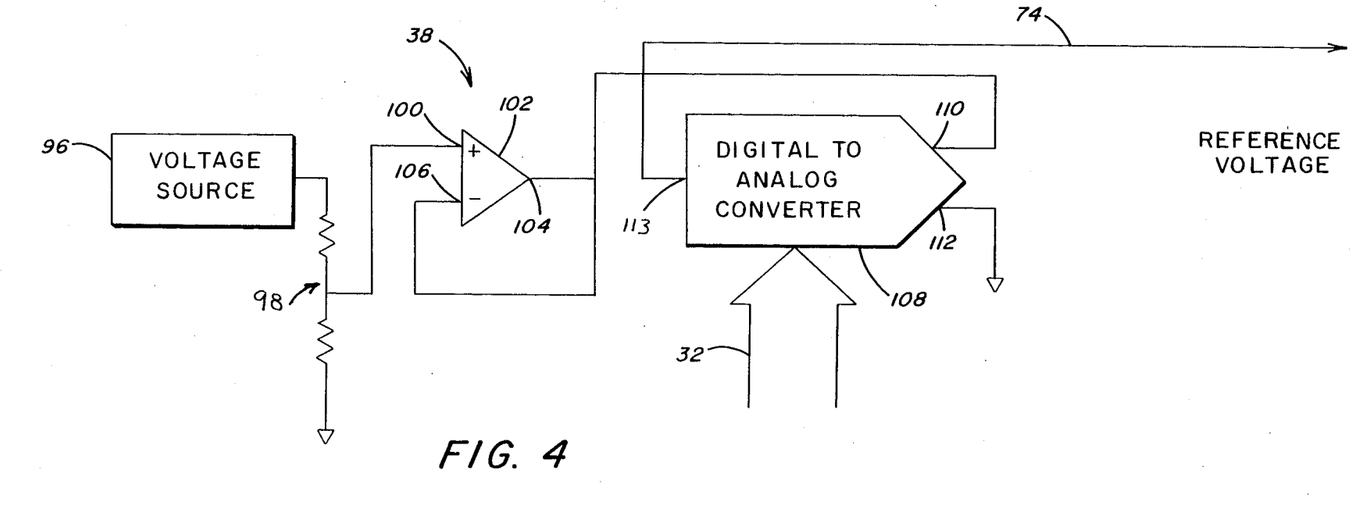
FIG. 4 is a view similar to FIG. 3 of the apparatus for controlling the reference voltage used in measuring the electrical current in each gas sensing element.

Now referring to FIGS. 3 and 4, there is illustrated the details of the programmable sensor voltage controller 36 and the programmable reference voltage controller 38 shown in FIG. 2 for measuring the electrical resistance associated with each gas sensor in the array 12. Through the instrumentation 14 shown in FIG. 1, the microcomputer 16 selects the value of the operating voltage maintained across each sensor 52. Also the microcomputer 16 can change the selected value of voltage at selected time intervals. The manner in which voltage is applied to a metal oxide semiconductor sensor affects the measured resistance response of the sensor. For example, the gas sensitivities, response time to step change in gas concentrations, and long-term stability of the response model parameters may be enhanced if the voltage is applied in a suitable manner. As illustrated in greater detail in FIGS. 6-8, each gas sensor 52 in the array 12 includes the substrate 54 provided with a film heater 55, preferably fabricated of platinum, on one side and electrodes 56 and 58 on the opposite side of the substrate 54.

Now referring to FIG. 3, there is illustrated the circuitry for providing a programmable voltage in accordance with the resistance measurement method used for the gas sensors 52 of the present invention. A programmable voltage is generated and maintained across each sensor 52 by a fixed reference voltage source 78 which is connected to a multiplying digital to analog converter 80 and an operational amplifier 82. A suitable multiplying converter for use with the present invention is available from Analog Devices, Inc. identified by part no. AD7542. Preferably the fixed voltage source 78 is a reference/regulator integrated circuit manufactured by Analog Devices, Inc., part no. AD580, to provide a fixed 2.500 plus or minus 0.001 volts as a fixed voltage reference. The source at 2.500 volts drives the 12 bit digital to analog converter 80 which is connected to the operational amplifier 82 to form a linear programmable voltage divider.

The converter 80 includes an input terminal 84 connected to the reference voltage source 78. An output terminal 86 of converter 80 is connected to the negative input terminal 88 of operational amplifier 82. Feedback terminal 90 is connected to output terminal 92. Output terminal 94 and input terminal 91 are connected to ground. Data from the microcomputer 16 is supplied through the input/output lines 32 to the converter 80.

With this arrangement the resulting programmable voltage from the output terminal 92 of the operational amplifier 82 is stable, accurate and has a range of 0 to negative 2.500 volts. The programmable voltage output from the operational amplifier 92 drives all the sensors 52 in the array 12 simultaneously. In the alternative each sensor 52 can be supplied with a preselected voltage distinct from the voltages applied to the other sensors 52. Accordingly the microcomputer 16 sets the desired sensor voltage by transmitting a digital to analog conversion count in the range 0 to 4095 which linearly corresponds to a programmed sensor voltage of 0 to negative 2.500 volts in incremental steps.

Now referring to FIG. 4 there is illustrated in detail the programmable reference voltage controller 38 diagrammatically shown in FIG. 2, and similar to the above described programmable sensor voltage controller 36 shown in FIG. 3. The reference voltage controller 38 generates an output signal representing a reference voltage to the comparator 48 shown in FIG. 2. A programmable reference voltage is generated by a fixed reference voltage source 96 which is connected through a resistance divider 98 to input terminal 100 of operational amplifier 102 having an output terminal 104 connected in a feedback circuit to negative input terminal 106. Output from the operation amplifier 102 is transmitted to a multiplying digital to analog converter 108 as shown in FIG. 4 at input terminal 110. Terminal 112 of the converter 108 is connected to ground. A suitable converter 108 is manufactured by Analog Devices Inc., part no. AD7542.

Input from the input/output port 20 of the microcomputer 16 is directed via the input/output lines 32 to the converter 108. In response to the input from the microcomputer 16, an output signal through conductor 74 from terminal 113 of converter 108 serves as a reference voltage input signal to the comparator 48 as shown in FIG. 2. In this manner a reference voltage is applied to the comparator 48 which is in turn compared to the respective output signals representing the current output of each gas sensor 52.

Temperature Control

Figure 5:
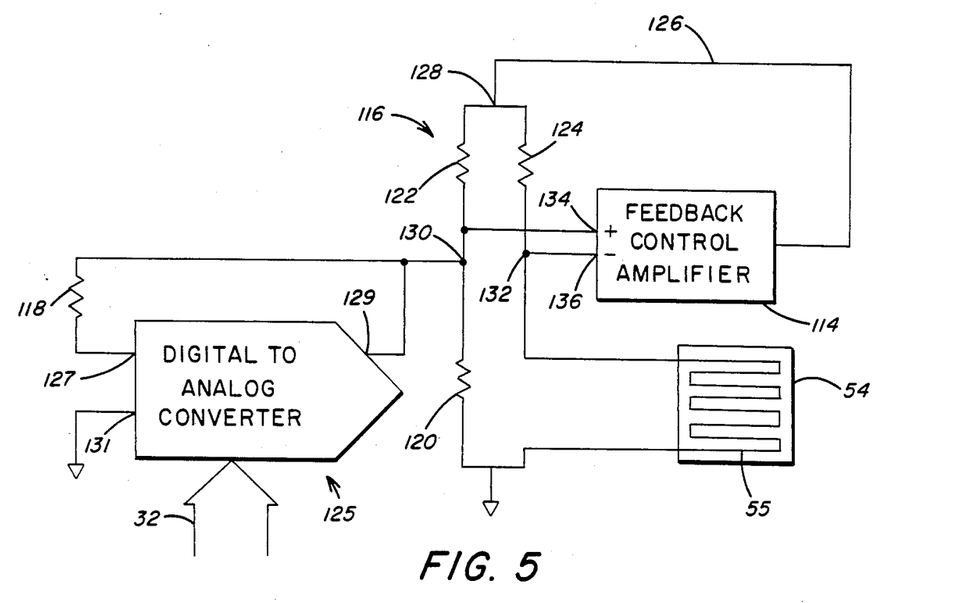
FIG. 5 is an electrical schematic of the apparatus for controlling the temperature of a respective sensor in the array at a preselected temperature in the gas detection operation.

Now referring to FIG. 5 there is illustrated the circuitry for raising the film heater 55 on the sensor substrate 54 to a preselected temperature by electrical current generated from the output of a feedback control amplifier 114. The substrate 54 provides effective heat transfer so that the platinum film heater 55 and the metal oxide semiconductor material are at substantially the same temperature.

As further illustrated in FIG. 5 a Wheatstone bridge generally designated by the numeral 116 is connected to the film heater 55 and feedback control amplifier 114. The Wheatstone bridge 116 includes as one of the resistance elements the platinum film heater 55 on the gas sensor substrate 54. A second resistance element is the resistor 124 connected by conductor 126 to amplifier 114, and the third resistance element is the resistor 122. The fourth resistance element is a combination of the fixed resistance values of resistors 118 and 120 in addition to the resistance provided by the multiplying digital to analog converter 125. A suitable converter 125 for use in the present invention is manufactured by Advanced Micro Devices Inc., part no. AM6080.

The converter 125 includes a positive reference input terminal 127 connected in a feedback loop through resistor 118 to an output terminal 129. A negative reference input terminal 131 is connected to ground. With this arrangement the converter 125 provides a programmable resistance for the Wheatstone bridge 116. Thus the converter operates as a reference resistor which is fixed at a preselected resistance. In the bridge 116 the resistance ratio of the film heater 55 to the resistor 124 is equal to the resistance ratio of the combined resistor 118, resistor 120, and converter 125 to the resistor 122. In operation the above described four resistance elements are maintained in balance by the negative feedback from amplifier 114.

The voltage at node 128 established by the amplifier 114 represents the greatly amplified difference between the input voltages at nodes 130 and 132 connected to terminals 134 and 136 respectively of amplifier 114. If a change in ambient conditions occurs, for example a decrease in ambient temperature, the temperature of the substrate 54 changes from its setpoint value to a slightly lower value. The heater film resistance also descreases slightly. Consequently the voltage at node 132 becomes slightly lower than the potential at node 130. The resulting voltage difference between nodes 130 and 132 is amplified by the amplifier 114 so that the potential at node 128 increases as do the voltages at nodes 130 and 132. The increased rate of heat generation in the heater film 55 restores the substrate temperature to its setpoint value, and the voltages at nodes 130 and 132 again become substantially equal. In this instance voltages at nodes 130 and 132 are higher than before the change in ambient conditions occurred.

With the above described arrangement the Wheatstone bridge 116 provides a self-adjusting process controlling for the temperature of the metal oxide semiconductor sensor 52. In one example of operation the platinum film heater 55 has a resistance of 10 ohms at 0° C. and 30 ohms at 600° C. The resistance of heater 55 varies approximately linearly with temperature over the range 0° C. to 600° C. For operation at 600° C. approximately 2 watts of power is dissipated. This power dissipation corresponds to a current of 240 milliampers and a voltage at node 132 of about 8 volts.

In operation the user through the microcomputer 16 identifies the particular gas or gases to be identified, as well as, the interference gases likely to be encountered by the gas sensor array 12. The microcomputer 16 sets the sensor operating temperatures to the appropriate values. The microcomputer 16 measures the sensor resistances and converts the values to digital form through an analog to digital converter and then calculates the respective target gas concentrations using a signal processing algorithm (deconvolution algorithm). The microcomputer 16 transmits as output to the user the gas concentration values and actuates the alarm 22 and display 26, if pre-established gas concentration thresholds are exceeded. Also the microcomputer 16 maintains in non-volatile memory the numerical model parameters for describing the response of each gas sensor 52 in the array 12 to each gas when operating at a selected temperature.

More gases can be detected than the number of gas sensors 52 present in the array 12 of gas sensors. This is accomplished by successively operating one or more gas sensors 52 at a plurality of preselected temperatures by the circuitry shown in FIG. 5 and discussed above to obtain from the resistance measurements the data required to execute the deconvolution algorithm by the microcomputer 16. For example, one sensor 52 can be successively operated at the temperatures of 400° C., 500° C., and 600° C. to determine the gas concentrations of three different gases.

The film heater 55 for each gas sensor 52 is operated up to temperatures of about 600° C. Preferably the film heater 55 is fabricated of platinum to insure precise and stable temperature control. This is essential for accurate deconvolution in which the electrical signals from the array 12 are analyzed by the computer 16 to produce a representation of the concentrations of the target gases detected in ambient air by the respective sensors 52.

In regard to the gas concentrations, the concentrations are determined in response to the measured resistances in the predetermined model equations discussed above. Preferably the method used to determine the gas concentrations is the conventional least-squares method. The algorithm that is used to perform the least-squares method is the known gradient-expansion algorithm which is extended for use with multiple independent variables. With this routine a superior convergence range is available when highly nonlinear equations, such as the model sensor equations, are used.

The measured gas concentrations are converted by the microcomputer 16 to an alpha-numeric readout at display 26. In the event of measurement of a gas concentration in excess of a predetermined threshold amount, a timer interrupt routine is actuated and an audible signal is generated by alarm 22 at a desired rate, for example once a second for 1/10 second intervals.

Power Requirements

Three voltage sources are needed to power the circuitry of the present invention. Positive and negative 12 volts are required for the instrumentation 14 and film heater 55. Positive 5 volts are supplied to the digital circuitry and microcomputer. Power consumption can also be reduced by substituting CMOS fabricated components for the microcomputer 16 and instrumentation 14. Overall the detection instrument 10 is powered by either D.C. batteries or an A.C. power adapter.

Sensor Construction

Figure 6:
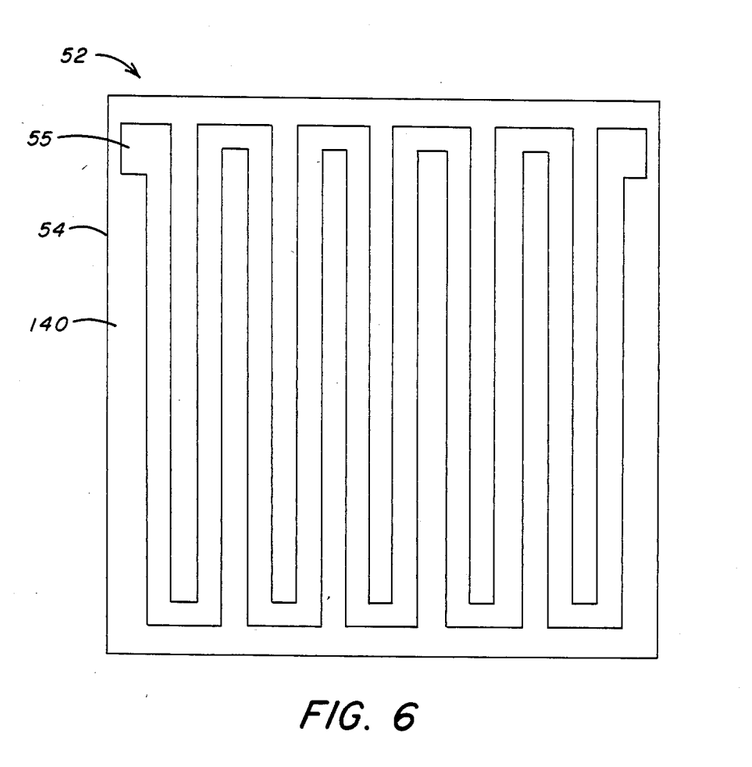
FIG. 6 is an enlarged plan view of the substrate of a gas sensor in accordance with the present invention, illustrating a platinum film heater positioned on one side of the substrate.
Figure 7:
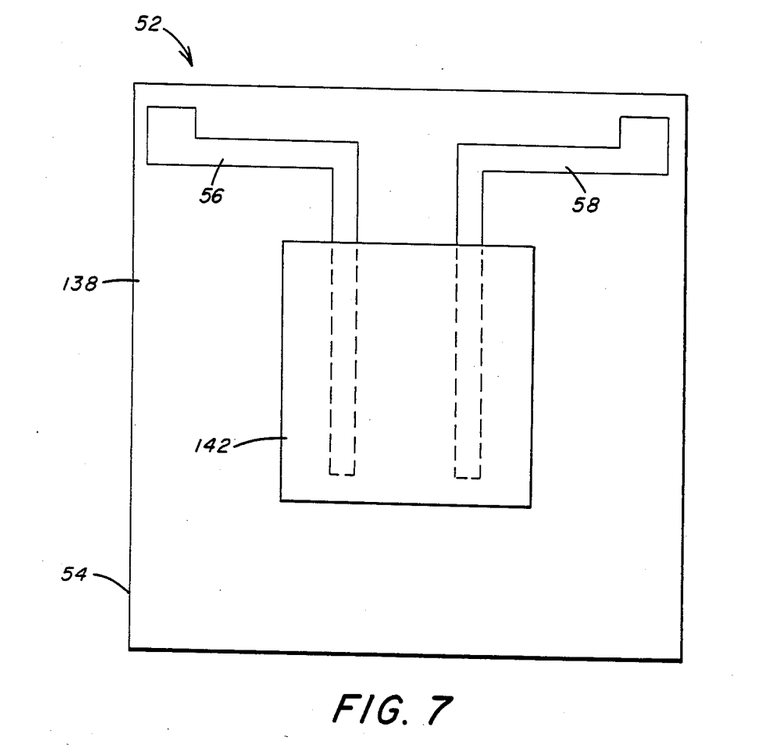
FIG. 7 is a top plan view of a gas sensor in accordance with the present invention, illustrating the substrate shown in FIG. 6 having a gas sensing material and sensor electrodes positioned on the side of the substrate opposite the platinum film heater.
Figure 8:
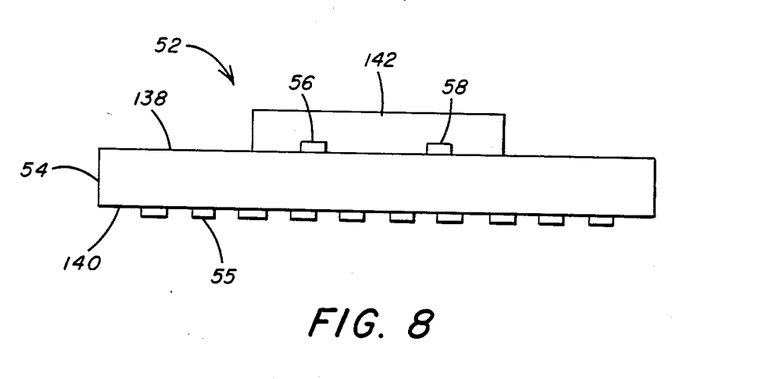
FIG. 8 is a view in side elevation of the gas sensor shown in FIG. 7, illustrating the gas sensing material and sensor electrodes on one surface of the substrate and the platinum film heater on the opposite surface of the substrate.

Now referring to FIGS. 6-8, there is illustrated an exemplary embodiment of the construction of a gas sensor 52 suitable for use in accordance with the present invention. It should be understood, however, that the present invention is not limited to gas sensors of the construction shown in FIGS. 6-8. Preferably the gas sensor substrate 54 is fabricated of alumina and includes a sensor side 138 shown in FIG. 7 and a heater side 140 shown in FIG. 6. On the sensor side 138 electrode paris 56 and 58 are connected to the substrate 54 and sensor material 142. The heating element 55 on the heater side 140 is preferably in the form of an elongated film of platinum.

In accordance with the present invention the gas sensor array 12 provides for low power consumption and fast response to changes in gas concentration. The array 12 also generates negligible response to common interference gases, such as alcohol or water vapor. The gas sensor array 12 includes individual gas sensors 52 each having a distinct gas response characteristic to a preselected target gas to be detected. Each gas sensor 52 includes sensing material supported on one side of a substrate 54 with the substrate 54 heated by a platinum film heater 55 on the opposite side of the substrate.

Each sensor 52 in the array 12 is calibrated for each of the target gases at each operating temperature. The numerical parameters which appear in the sensor gas response model equations are known and stored in the memory of the microcomputer 16. Preferably each gas sensor 52 includes a metal oxide semiconductor material as described in greater detail in conpending U.S. application Ser. No. 017,838.

With the above described arrangement heat can escape from the sensor substrate 54 to the surrounding atmosphere by conduction, radiation, and convective transport through the air. To reduce power consumption the substrate can be utilized in combination with heat reflectors and thermal insulation. Also by reducing the substrate area finer diameter leads can be utilized due to the decreased mass of the sensor.

Deconvolution Algorithm

Figure 9:
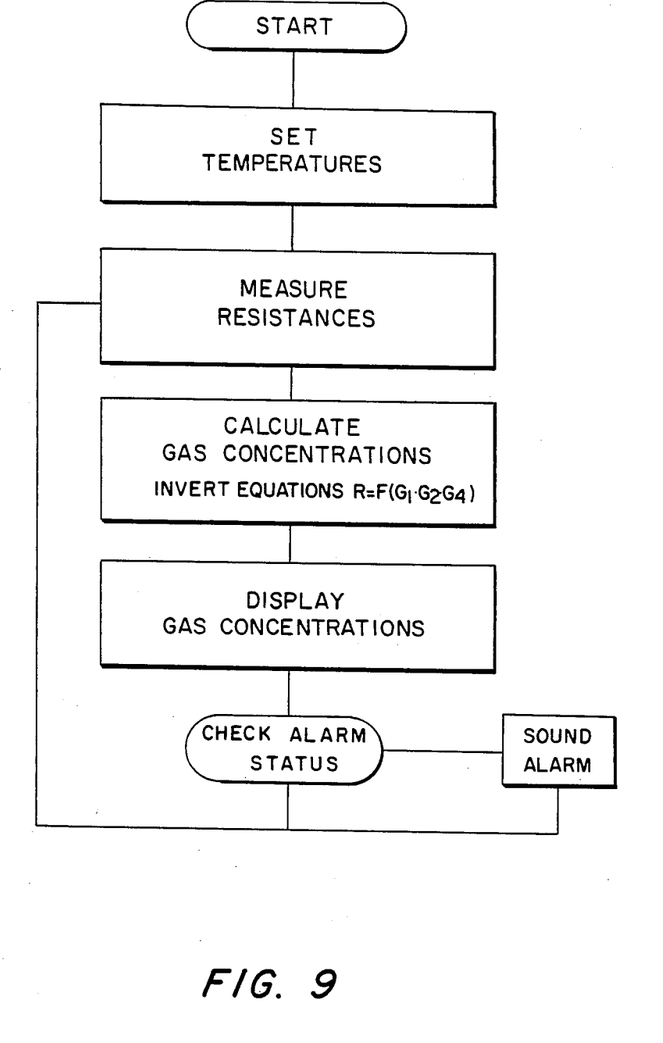
FIG. 9 is a diagrammatic illustration of the sequence of steps that are preformed in measuring a plurality of gases in air by the gas detection instrument of the present invention.

Now referring to FIG. 9 there is graphically illustrated the sequence of steps performed by the gas detection instrument 10 of the present invention to determine the concentration of selected gases in ambient air. The gas concentrations are determined by the solution of the predetermined model equations and the measured values of the resistances of the gas sensors. The method of solution is based on the known least squares technique. The algorithm that implements the least squares technique combines features of the known Newton linearization method with the features of the known gradient search method. This algorithm is known as the gradient expansion algorithm. The combination of these two methods provides for a deconvolution procedure having desired convergence properties. The deconvolution program for methane and carbon monoxide using the gradient-expansion algorithm converges to the correct answer given any starting point from 1 ppm to $10^6$ ppm.

In one embodiment once the known parameters have been defined for the model equations used, the gas detection instrument automatically performs the steps of measuring the resistances and provides a numerical readout of the gas concentrations. With the temperatures of the sensor film heaters being set, the resistances of each gas sensor are measured and these resistance values are used to solve the non-linear equations using the gradient-expansion algorithm.

Once the resistances have been measured the quantitative values of the gas concentrations are calculated. The gas concentrations are digitally displayed. Based on the calculated concentrations the measured values are compared to threshold values. If the threshold values are exceeded, then an audio/visual alarm is actuated. If the gas concentrations are below the threshold amounts, then the above steps are repeated to determine if the resistance values associated with the gas sensors have changed. The resistance measurements are taken again and the deconvolution process is repeated to determine the gas concentrations. If there is no change, then the same display is generated. The sequence is repeated at selected intervals, for example every thirty seconds.

According to the provision of the patent statues we have explained the principle, preferred construction and mode of operation of our invention and have illustrated and described what we now consider to represent its best embodiments. However, it should be understood, that within the scope of the appended claims, the invention may be practiced otherwise than as specifically illustrated and described.

We claim:

1. An instrument for simultaneously quantifying the concentrations of a number of gases present in an oxygen containing atmosphere comprising,
   a computer for providing a quantitative presentation of the gas concentrations,
   a number of semiconductor gas sensing elements at least equal in number to the number of gases to be detected,
   said gas sensing elements each having a predetermined quantifiable response characteristic differing from the response characteristic of the other of said gas sensing elements in response to at least one of the gases to be detected,
   temperature control means for maintaining the temperature of each gas sensing element at a selected value by compensating for thermal variations in the surrounding environment,
   said temperature control means coupled to and responsive to said computer to maintain each of said gas sensing elements at a selected one of a number of operating temperatures,
   measurement means connected to each of said gas sensing elements for generating an electrical signal representing the response of each of said respective gas sensing elements to each of the gases to be detected,
   said measurement means electrically connected to said computer, and
   said computer including means for converting said electrical signals from said measurement means to a digital representation.

2. An instrument as set forth in claim 1 in which, said measurement means is responsive to said computer so that a selected one of a plurality of voltages is maintained across each of said gas sensing elements.

3. An instrument as set forth in claim 1 which includes,
   voltage control means for selecting the voltage maintained across each gas sensing element,
   said voltage control means electrically connected to said computer, and
   said computer having means for measuring the electrical current through each of said gas sensing elements.

4. An instrument as set forth in claim 1 in which, said measurement means applies a preselected voltage to each of said gas sensing elements.

5. An instrument as set forth in claim 1 in which, said temperature control means includes a Wheatstone bridge,
   said Wheatstone including a plurality of resistors, and
   one of said resistors having a resistance value which is programmable to correspond to a selected operating temperature of each of said gas sensing elements in a range of from ambient temperature to 600° C.

6. A method for maintaining a quantifiable relationship between the response of a gas sensing element and the concentration of a target gas to be detected comprising the steps of,
   supporting a gas sensing element on a substrate,
   positioning a platinum film element on the substrate,
   passing current through the platinum film element to heat the substrate and raise the gas sensing element to a preselected temperature for generating a responsive signal indicating the concentration of a selected target gas in an oxygen containing atmosphere,
   setting the resistance of the platinum film element at a preselected set-point value, and
   controlling the current through the platinum film element to adjust the rate of heat generation in the platinum film element to maintain the resistance of the platinum film element at a preselected setpoint value to obtain a quantitative relationship between the signal from said gas sensing element and the concentration of the target gas independent of any variations in the surrounding environment.

7. A method as set forth in claim 6 which includes,
   maintaining the resistance of the platinum film element at a preselected magnitude to maintain the temperature of the substrate at a preselected magnitude independent of any variations in the surrounding environment.

8. A method as set forth in claim 6 which includes,
   the platinum film element serving as a substrate heating element and a substrate temperature transducer.

9. A method as set forth in claim 6 which includes,
   controlling the resistance of the platinum film element by a Wheatstone bridge circuit connected thereto, and
   providing as one of a plurality of resistors in the Wheatstone bridge a digital to analog converter having a resistance value selectable to maintain the temperature of the platinum film heater and substrate at a selected one of a plurality of discrete temperatures in the range from ambient temperature to 600° C.

10. A method as set forth in claim 6 which includes,
    measuring the concentration of a selected gas in air by heating the gas sensing element to a preselected temperature on the substrate,
    varying the resistance of the platinum film element to change the temperature of the substrate and set the temperature of the gas sensing element at selected discrete magnitude in the range from ambient temperature to 600° C., and
    individually measuring the concentration of a plurality of discrete gases in air by setting the temperature of the gas sensing element to a preselected temperature in said range corresponding to the desired gas to be detected.

11. A system for simultaneous detection of the quantifiable concentration of a number of target gases in an oxygen containing atmosphere comprising, a number of gas sensors at least equal in number to the number of gases to be detected, each of said gas sensors including a layer of gas sensing material, means for supporting each layer of gas sensing material, a pair of metallic electrodes in contact with each layer of gas sensing material, means for supplying a voltage to said electrodes to apply a voltage to said gas sensing material, a resistance measuring device connected to said electrodes, said resistance measuring device converting the values of the electrical resistances of said electrodes to a plurality of digital output signals, signal processing means for receiving said digital output signals from said resistance measuring device, means for transmitting the value of said electrical resistances in the form of said digital output signals to said signal processing means, and said signal processing means converting said digital output signals to a quantifiable value of the concentrations of the target gases detected.

12. A system as set forth in claim 11 which includes,
an analog to digital converter for supplying digital input to said signal processing means for determining the resistances of each of said layers of gas sensing material in response to the voltage applied thereto.

13. A system as set forth in claim 11 which includes,
voltage reference means for maintaining a fixed voltage reference across said electrodes,
means for supplying digital input to said signal processing means for determining the resistance of said electrodes and setting a desired reference voltage by transmitting a digital signal to said voltage reference means.

14. A system as set forth in claim 11 in which,
each layer of gas sensing material includes a semiconductor metal oxide material,
said means for supporting said layers of gas sensing material including a substrate in contact with said electrodes, and
a platinum film heater positioned on said substrate oppositely of each of said layers of gas sensing material.

15. A gas detecting instrument comprising,
a number of electrically insulating substrates,
at least a single pair of electrodes positioned on each of said substrates,
a layer of gas sensing material in contact with said electrodes on each of said substrates,
a voltage source connected to said electrodes,
means for controlling the temperature of each of said gas sensing materials at preselected values,
means for measuring the electrical resistance of said gas sensing material in response to a number of gases to be detected in air at least equal in number to the number of said single pair of electrodes, an analog to digital converter connected to said means for measuring the electrical resistance for converting the value of the measured electrical resistance to a digital representation, and a signal processor connected to said analog to digital converter for receiving the measurement of the electrical resistance in said digital representations and computing a quantifiable value of the gas concentrations detected from the electrical resistance measurements.

16. A gas detecting instrument as set forth in claim 15 which includes,
means for controlling the voltage applied across each layer of said gas sensing material, and
means for adjusting the temperature of each of said substrates to discrete selectable temperatures.

17. A gas detecting instrument as set forth in claim 15 in which,
said means for setting the temperature of said gas sensing material is a temperature transducer including a platinum heating element.

18. A gas detecting instrument as set forth in claim 15 in which,
said means for controlling temperature includes a Wheatstone bridge circuit,
a platinum film heater electrically connected to each substrate and to said circuit,
said circuit including a resistor element selectively adjustable to a preselected resistance to maintain said substrate at a preselected temperature, and
a digital to analog converter electrically connected to said signal processor for selecting the resistance of said resistor element corresponding to a preselected temperature at which each of said layers of gas sensing materials are to be maintained.

19. A gas detecting instrument as set forth in claim 15 which includes,
means for maintaining a selected voltage to said electrodes and applied to each of said layers of gas sensing material, and
said signal processing means measuring the current flowing through each of said layers of gas sensing material.

20. A gas detecting instrument as set forth in claim 15 in which said means for controlling the temperature includes,
a platinum film heater connected to each of said insulating substrates for heating said gas sensing material thereon, and
said means for selectively controlling the temperature of said respective platinum film heaters and accordingly said layers of gas sensing material by maintaining the electrical resistance of said platinum film heaters at preselected fixed values.

* * * * *

UNITED STATES PATENT AND TRADEMARK OFFICE
CERTIFICATE OF CORRECTION

PATENT NO. : 4,847,783

DATED : Jul. 11, 1989

INVENTOR(S) : Grace et al.

It is certified that error appears in the above-identified patent and that said Letters Patent is hereby corrected as shown below:

At [56] References Cited, change "The Use of Multi-Sensors Systems in Monitoring Hazardous Atmosphers" to -- "The Use of Multi-Sensors Systems in Monitoring Hazardous Atmospheres" --.

At [56] References Cited, at "Multidimensional Sensors for Gas Analysis" change "R. Miller" to -- R. Muller --.

At [56] References Cited, at Attorney, Agent, or Firm, change "Ingersoll Buchanan" to -- Buchanan Ingersoll --.

Column 1, line 29, change "value" to -- values --.

Column 10, line 2, change "paris" to -- pairs --.

Column 10, line 24, change "conpending" to -- co-pending --.

Column 11, line 10, change "statues" to -- statutes --.

Column 11, line 50, after "representation" delete ',' and insert -- . --.

UNITED STATES PATENT AND TRADEMARK OFFICE
CERTIFICATE OF CORRECTION

PATENT NO. : 4,847,783
DATED : Jul. 11, 1989
INVENTOR(S) : Grace et al.

It is certified that error appears in the above-identified patent and that said Letters Patent is hereby corrected as shown below:

Column 12, line 7, after "range" delete -- of --.

Signed and Sealed this

Eighth Day of May, 1990

*Attest:*

HARRY F. MANBECK, JR.

*Attesting Officer*      *Commissioner of Patents and Trademarks*